(12) United States Patent
Coggan et al.

(10) Patent No.: US 7,544,842 B1
(45) Date of Patent: Jun. 9, 2009

(54) PROCESS FOR THE PREPARATION OF ARYL-DIAMINES

(75) Inventors: Jennifer A. Coggan, Cambridge (CA); Matthew A. Heuft, Oakville (CA); Nan-Xing Hu, Oakville (CA)

(73) Assignee: Xerox Corporation, Norwalk, CT (US)

( * ) Notice: Subject to any disclaimer, the term of this patent is extended or adjusted under 35 U.S.C. 154(b) by 0 days.

(21) Appl. No.: 11/952,555

(22) Filed: Dec. 7, 2007

(51) Int. Cl.
*C07C 211/00* (2006.01)
(52) U.S. Cl. ...................................... 564/307
(58) Field of Classification Search ........................ None
See application file for complete search history.

(56) References Cited

U.S. PATENT DOCUMENTS

| | | | | |
|---|---|---|---|---|
| 4,588,666 A | * | 5/1986 | Stolka et al. | 430/58.8 |
| 4,935,487 A | * | 6/1990 | Yanus et al. | 528/203 |
| 4,983,781 A | * | 1/1991 | Desmurs et al. | 570/210 |
| 2006/0111588 A1 | | 5/2006 | Bender et al. | |
| 2007/0100164 A1 | | 5/2007 | Coggan et al. | |

OTHER PUBLICATIONS

Creason et al, The Journal of Organic Chemistry, Electrochemical and Spectroscopic Studies of Cation Radicals. I. Coupling Rates of 4-Substituted Triphenylaminium Ion, 1972, 37(26), pp. 4440-4445.*

Thayumanavan et al, Chemical Materials, Synthesis of Unsymmetrical Triarylamines for Photonic Applications via One-Pot Palladium-Catalyzed Aminations, 1997, 9, pp. 3231-3235.*
Litke et al, Angewandte Chemie, International Edition, A convenient and General Method for Pd-Catalyzed Suzuki Cross-Couplings of Aryl Chlorides and Arylboronic Acids, 1998, pp. 3387-3388.*
Greene, Protective Groups in Organic Chemistry, 1981, John Wiley & Sons, New York, pp. 14-16.*
U.S. Appl. No. 11/940,718, filed Nov. 15, 2007 to Coggan.
U.S. Appl. No. 11/734,593, filed Apr. 12, 2007 to Coggan et al.
U.S. Appl. No. 11/563,931, filed Nov. 28, 2006 to Bender et al.
U.S. Appl. No. 11/563,873, filed Nov. 28, 2006 to Bender et al.
Taillefer et al., "Efficient Iron/Copper Co-Catalyzed Arylation of Nitrogen Nucleophiles," Angew. Chem. Int. Ed. 2007, 46, pp. 934-936.
Chen et al., "Ni(II)-(σ-Aryl) Complex: A Facile, Efficient Catalyst for Nickel-Catalyzed Carbon-Nitrogen Coupling Reactions," J. Org. Chem. 2007, 72, pp. 6324-6327.
Harris et al., "One-Pot Synthesis of Unsymmetrical Triarylamines from Aniline Precursors," J. Org. Chem. 2000, 65, pp. 5327-5333.

* cited by examiner

*Primary Examiner*—Paul A Zucker
(74) *Attorney, Agent, or Firm*—Oliff & Berridge, PLC

(57) ABSTRACT

A process for forming a N,N'-diaryl-N,N'-di(hydroxyaryl)-aryl-diamine compound includes reacting a halogenated aryl compound with an etherified diarylamine in the presence of a catalyst, then deprotecting the resulting N,N'-diaryl-N,N'-di(alkyl-oxyaryl)-aryl-diamine to form the N,N'-diaryl-N,N'-di(hydroxyaryl)-aryl-diamine.

17 Claims, 2 Drawing Sheets

PROCESS FOR THE PREPARATION OF ARYL-DIAMINES

TECHNICAL FIELD

This disclosure is generally directed to improved chemical processes for the synthesis of aryl-diamines. In particular, this disclosure provides a two-step method for producing N,N'-((hydroxy)$_m$-diaryl)-N,N'-((hydroxy)$_n$-diaryl)-aryl-diamine compounds, wherein an halogenated aryl compound is reacted with a diarylamine having a protected oxygen functional group, then the resulting product is reacted with a deprotecting agent to form alcohol groups from the other groups.

RELATED APPLICATIONS

Commonly assigned, U.S. patent application Ser. No. 11/940,718 filed Nov. 15, 2007, describes processes for the synthesis of hydroxyl triarylamine compounds comprising reacting a halogenated aryl aldehyde with an aldehyde protecting agent, reacting the halogenated protected aryl aldehyde with an arylamine, then deprotecting the resulting product and reducing the aldehyde groups to alcohol groups to form a dihydroxyl triarylamine.

Commonly assigned, U.S. patent application Ser. No. 11/734,593 filed Apr. 12, 2007, describes a process for forming a triarylamine compound comprising reacting a halogenated aryl alcohol with an alcohol protecting agent and a first base to form a halogenated protected aryl alcohol compound, and reacting the halogenated protected aryl alcohol compound with an amine in the presence of a suitable catalyst and a second base.

Commonly assigned, U.S. patent application Ser. No. 11/563,931 filed Nov. 28, 2006, describes a process for forming a triaylamine compound, comprising reacting an aniline and an arylchloride in the presence of a palladium ligated catalyst and a base.

Commonly assigned, U.S. patent application Ser. No. 11/563,873 filed Nov. 28, 2006, describes a process for forming a diarylamine compound, comprising reacting an aniline and an arylbromide in the presence of a palladium ligated catalyst and a base.

Commonly assigned, U.S. patent application Ser. No. 11/263,671 filed Nov. 1, 2005, describes a process for the preparation of a tertiary arylamine compound, comprising reacting an arylhalide and an arylamine in an ionic liquid in the presence of a catalyst.

Commonly assigned, U.S. patent application Ser. No. 10/992,690 filed Nov. 22, 2004, describes a process for forming a tertiary arylamine compound, comprising reacting an arylbromide and an arylamine.

The appropriate components and process aspects of each of the foregoing, such as the arylamine precursor materials, may be selected for the present disclosure in embodiments thereof. The entire disclosures of the above-mentioned applications are totally incorporated herein by reference.

BACKGROUND

Image-forming devices such as copiers, printers and facsimiles include known electrophotographic systems in which charging, exposure, development, transfer, etc., are carried out using electrophotographic photoreceptors.

Such photoreceptors are known to include several layers, generally including: a substrate, an undercoating layer, an intermediate layer, an optional charge blocking layer, a charge generating layer over an undercoating layer and/or a blocking layer, a charge transport layer and an optional protective overcoat layer. These layers can be in a variety of orders to make up a functional device, and sometimes multiple layers can be combined in a single or mixed layer.

In the charge transport layer and the optional protective overcoat layer, hole transport molecules may be dispersed in a polymer binder. The hole transport molecules provide hole or electron transport properties, while the electrically inactive polymer binder provides mechanical properties.

Imaging members are generally exposed to repetitive electrophotographic cycling, which subjects the exposed charge transport layer or protective overcoat layer thereof to mechanical abrasion, chemical attack and heat. This repetitive cycling leads to gradual deterioration in the mechanical and electrical characteristics of the exposed charge transport layer.

In light of this deterioration, one type of protective overcoat layer has been used to provide increased crack, abrasion and scratch resistance of the photoreceptor when the photoreceptor is in a belt configuration. The layer is generally made up of three main components: a polyol binder, a melamine-formaldehyde curing agent and a hole transport material such as N,N'-diphenyl-N,N'-bis(3-hydroxyphenyl)-[1,1':4'1"-terphenyl]-4,4"-diamine.

The production of a number of N,N'-diaryl-N,N'-di(hydroxyaryl)-aryl-diamine compounds, such as N,N'-diphenyl-N,N'-bis(3-hydroxyphenyl)-[1,1':4'1"-terphenyl]-4,4"-diamine that is useful as the hole transport material in electrophotographic photoreceptors, often involves synthesis of intermediate materials which are generally costly and/or time-consuming to produce, and some of which involve a multi-step process.

Certain N,N'-diaryl-N,N'-di(hydroxyaryl)-aryl-diamine compounds may be produced by reaction of a diarylamine with an aryliodide under traditional Ullmann conditions (copper catalyst, high temperature, long reaction time) or the so-called ligand-accelerated Ullmann reaction that uses lower reaction temperatures but is still limited to the use of aryliodides. Aryliodides tend to be very expensive reagents. Furthermore, both of these reactions usually require lengthy and costly purification processes. These drawbacks, while nominal in a laboratory scale, pose significant challenges in scaling up a reaction to commercial level.

Accordingly, improved processes providing safe, cost-effective, and efficient methods for N,N'-((hydroxyl)$_m$-diaryl)-N,N'-((hydroxyl)$_n$-diaryl)-aryl-diamine production are desired.

SUMMARY

The present disclosure addresses these and other needs, by providing an improved method for the preparation of N,N'-((hydroxyl)$_m$-diaryl)-N,N'-((hydroxyl)$_n$-diaryl)-aryl-diamine compounds, where m and n are integers each having a value from 0 to 2 inclusive and the value of m+n is at least 1. More particularly, this disclosure provides an improved method of producing N,N'-((hydroxyl)$_m$-diaryl)-N,N'-((hydroxyl)$_n$-diaryl)-aryl-diamine compounds by the reaction of a halogenated aryl compound (such as a halogenated terphenyl) with a diarylamine having a protected oxygen functional group (such as methoxydiphenylamine), then the resulting product is reacted with a deprotecting agent to form a N,N'-((hydroxyl)$_m$-diaryl)-N,N'-((hydroxyl)$_n$-diaryl)-aryl-diamine compound.

DETAILED DESCRIPTION OF EMBODIMENTS

Figure 1:
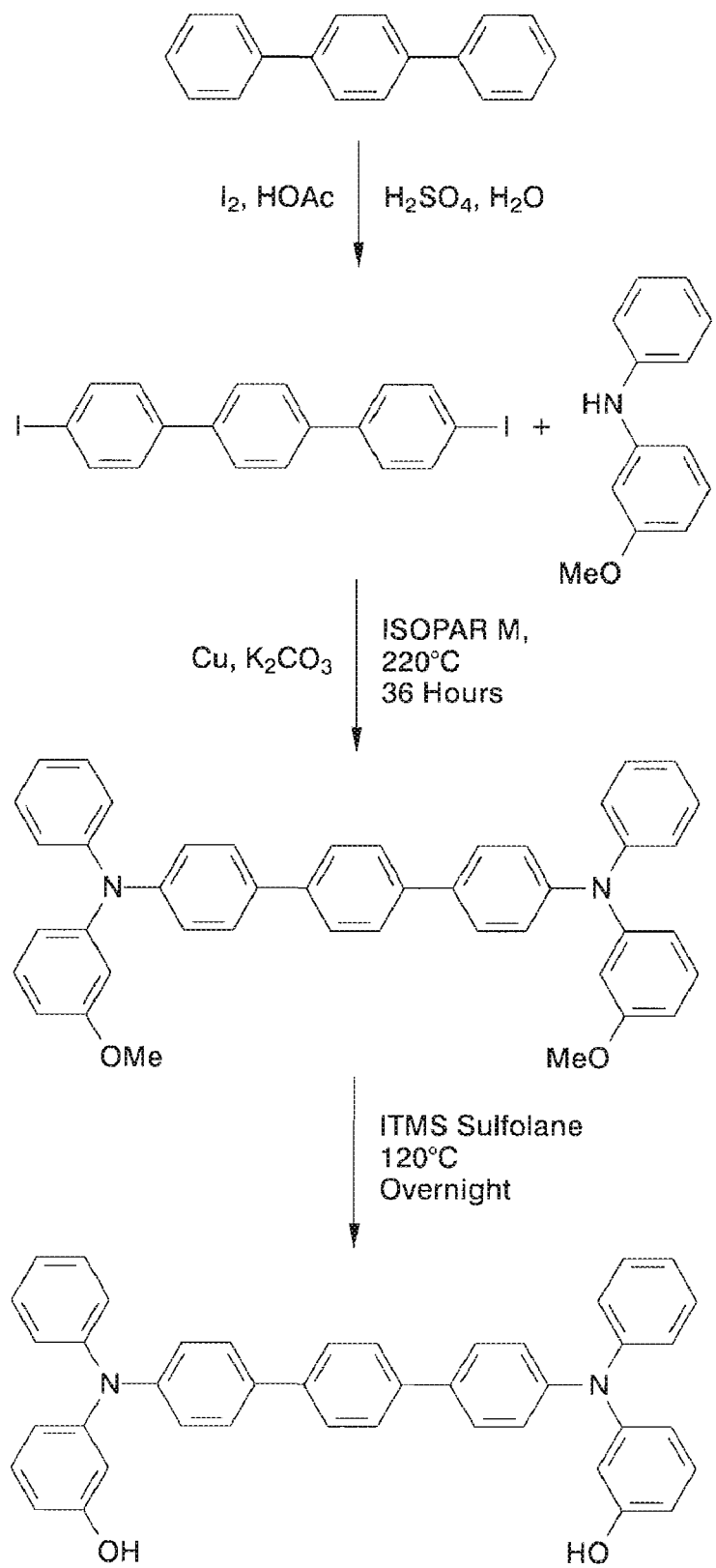
FIG. 1 represents a conventional process for producing a N,N'-((hydroxyl)$_m$-diaryl)-N,N'-((hydroxyl)$_n$-diaryl)-aryldiamine compound.

This disclosure is not limited to particular embodiments described herein, and some components and processes may be varied by one of ordinary skill in the art, based on this disclosure. The terminology used herein is for the purpose of describing particular embodiments only, and is not intended to be limiting.

In this specification and the claims that follow, singular forms such as "a," "an," and "the" include plural forms unless the content clearly dictates otherwise. In addition, reference may be made to a number of terms that shall be defined as follows:

The term "aryl" refers, for example, to monocyclic or fused-ring polycyclic (i.e., rings which share adjacent pairs of carbon atoms) carbocyclic aromatic ring systems having about 6 to about 20 carbon atoms or more, such as phenyl, naphthyl, anthrycyl, and the like. Optionally, these groups may be substituted with one or more independently selected substituents, including alkyl, alkenyl, alkoxy, hydroxyl, nitro and additional aryl groups. "Aryl" also includes heteroaryl groups, such as pyrimidine or thiophene.

The term "arylamine" refers, for example, to moieties containing both aryl and amine groups. Exemplary arylamine groups have the structure Ar-NRR', in which Ar represents an aryl group and R and R' are groups that may be independently selected from hydrogen and substituted and unsubstituted alkyl, alkenyl, aryl, and other suitable functional groups.

"Amine" refers, for example, to an alkyl moiety in which one or more of the hydrogen atoms has been replaced by an —NH$_2$ group. The term "lower amine" refers, for example, to an alkyl group of about 1 to about 6 carbon atoms in which at least one, and optionally all, of the hydrogen atoms has been replaced by an —NH$_2$ group.

The phrase "a diarylamine having a protected oxygen functional group" refers to a diarylamine having the structure (Ar$^1$)(Ar$^2$)NH in which at least one of Ar$^1$ and Ar$^2$ has at least one oxygen based functional group, that has been protected with a suitable protecting agent, as a substituent. For example, protected oxygen functional groups include ethers, acetals, and silyl ethers. The particular protected oxygen functional group is chosen to withstand subsequent reactions, after which the protecting group is removed. In embodiments, the oxygen protecting group can be an alkyl group, a tetrahydropyranyl group, or a trialkylsilyl group.

An improved two-step process for producing N,N'-((hydroxyl)$_m$-diaryl)-N,N'-((hydroxyl)$_n$-diaryl)-aryl-diamine compounds, directly from a halogenated aryl and a etherified diarylamine is provided.

The results surrounding this process were very unexpected in that the two-step process proceeding from the aryl compound and an etherified diarylamine to the desired N,N'-((hydroxyl)$_m$-diaryl)-N,N'-((hydroxyl)$_n$-diaryl)-aryl-diamine, proceeded easily and can be scaled-up to commercial scale. This process can be used in place of the process that uses an Ullmann reaction. The Ullmann reaction pathway generally suffers from insolubility of intermediates, lengthy reactions times, high reaction temperatures and difficult purification procedures. Therefore, the disclosed process is very practical and applicable to the preparation of N,N'-((hydroxyl)$_m$-diaryl)-N,N'-((hydroxyl)$_n$-diaryl)-aryl-diamine compounds on an industrial scale since the present two-step reaction produces the desired compound in a short reaction time with high purity.

Figure 2:
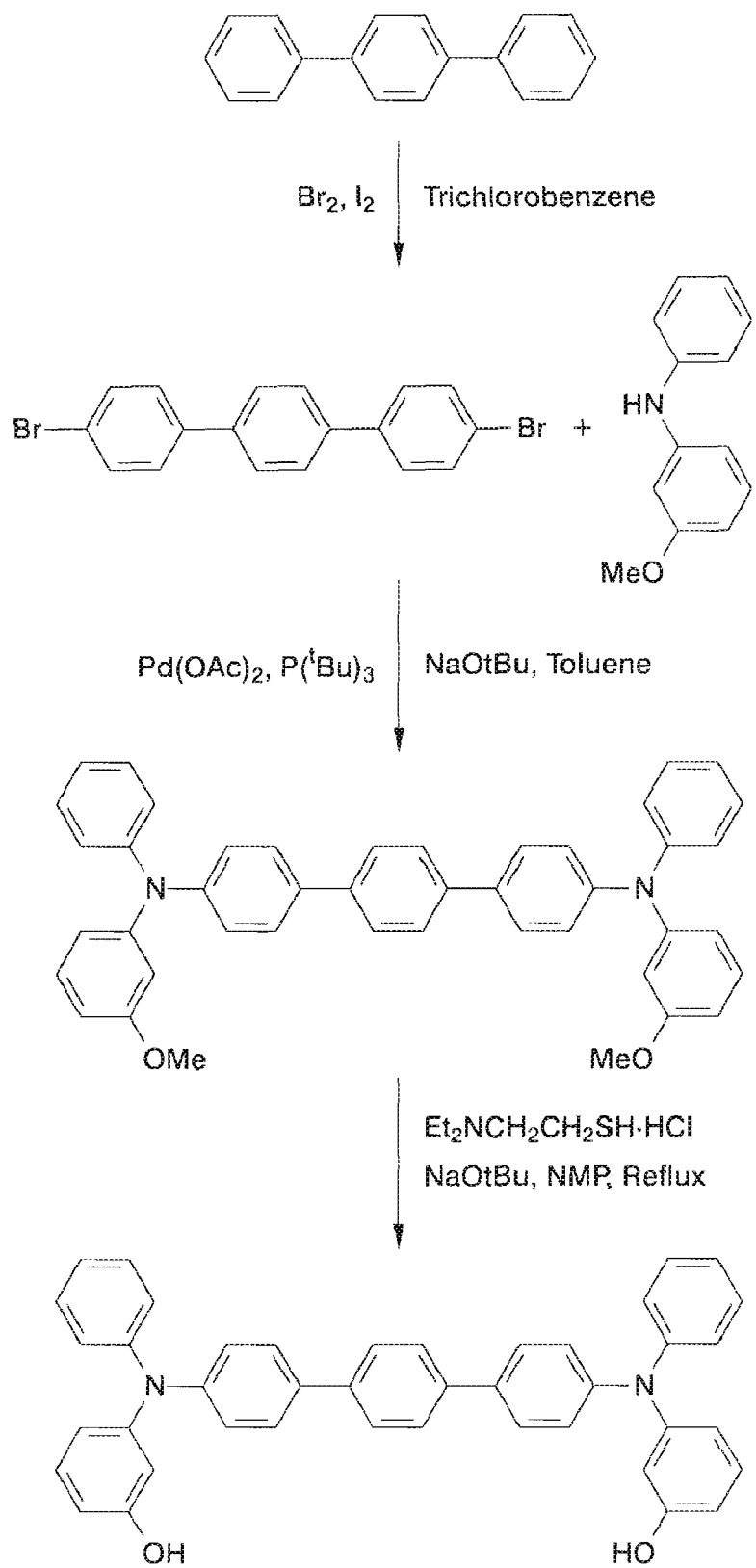
FIG. 2 represents processes for producing an exemplary N,N'-((hydroxyl)$_m$-diaryl)-N,N'-((hydroxyl)$_n$-diaryl)-aryldiamine compound according to the disclosure, including the precursor step of halogenating an aryl compound.

This improved process is now described in detail. Compare, for example, FIG. 1, which shows a conventional process for preparing a N,N'-((hydroxyl)$_m$-diaryl)-N,N'-((hydroxyl)$_n$-diaryl)-aryl-diamine, with FIG. 2, which shows an embodiment of the present processes for preparing a N,N'-((hydroxyl)$_m$-diaryl)-N,N'-((hydroxyl)$_n$-diaryl)-aryl-diamine.

In general, the process of the present disclosure can be represented as:

(1) X—Ar$^1$—X+((R$^1$O)$_m$—Ar$^2$)—NH—(Ar$^3$—(OR$^1$)$_n$) →((R$^1$O)$_m$—Ar$^2$)(Ar$^3$—(OR$^1$)$_n$)—N—Ar$^1$—N—((R$^1$O)$_n$—Ar$^3$)(Ar$^2$—(OR$^1$)$_m$)

(2) ((R$^1$O)$_m$—Ar$^2$)(Ar$^3$—(OR$^1$)$_n$)—N—Ar$^1$—N—((R$^1$O)$_n$—Ar$^3$)(Ar$^2$—(OR$^1$)$_m$)→((HO)$_m$—Ar$^2$)(Ar$^3$—(OH)$_n$)—N—Ar$^1$—N—((HO)$_n$—Ar$^3$)(Ar$^2$—(OH)$_m$)

where m is an integer having a value from 0 to 2 inclusive; n is an integer having a value from 0 to 2 inclusive, where the value of m+n is at least 1; X represents a halogen; R$^1$ represents an alkyl group such as from 1 to about 20 carbon atoms or from 1 to about 10 carbon atoms, a tetrahydropyranyl group, or a trialkylsilyl group; and Ar$^1$, Ar$^2$ and Ar$^3$ independently represent aryl groups.

Ar$^1$, Ar$^2$ and Ar$^3$ can be any known substituted or unsubstituted aromatic component or a substituted or unsubstituted aryl group having from 2 to about 15 conjugate bonded or fused benzene rings and could include, but is not limited to, phenyl, naphthyl, anthryl, phenanthryl, and the like. The substituents on Ar$^1$, Ar$^2$ or Ar$^3$ can be suitably selected to represent hydrogen, a halogen, an alkyl group having from 1 to about 20 carbon atoms, a hydrocarbon radical having from 1 to about 20 carbon atoms, an aryl group optionally substituted by one or more alkyl groups, an alkyl group containing a heteroatom such as oxygen, nitrogen, sulfur, and the like, having from 1 to about 20 carbon atoms, a hydrocarbon radical containing a heteroatom such as oxygen, nitrogen, sulfur, and the like, having from 1 to about 20 carbon atoms, an aryl group containing a heteroatom such as oxygen, nitrogen, sulfur, and the like, optionally substituted by one or more alkyl groups, and the like. Where the substituent on Ar$^1$, Ar$^2$ or Ar$^3$ is an aryl group, Ar$^1$, Ar$^2$ or Ar$^3$ can be for example biphenyl, terphenyl, and the like.

In exemplary embodiments, Ar$^1$ can be, for example, -Phenyl-, -Phenyl-Phenyl-, -Phenyl-Phenyl-Phenyl-, or the like. Likewise, in such embodiments, Ar$^2$ can be, for example, of the following structures:

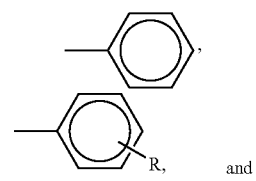

, and

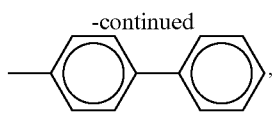

where R represents an optional one or more substituents on the phenyl ring, such as —CH$_3$, —C$_2$H$_5$, —C$_3$H$_7$, and —C$_4$H$_9$.

Prior to the first step, a halogenated aryl compound is provided. The halogenated aryl compound can be purchased pre-made, or manufactured according to any of various processes known in the art. For example, terphenyl can be brominated with the use of bromine with a trace of iodine in trichlorobenzene at 100° C. The halogenated aryl compound may be, for example, a single benzene ring or a compound comprised of a series of phenyl groups, for example a bi- or ter- phenyl, bonded to a halogen. Such a reaction can take place at about 100° C. for a period of about 1 hour. Suitable reaction conditions further include, for example, the use of a solvent and the presence of iodine as a catalyst. The solvent may be, for example trichlorobenzene, or other appropriate solvents.

In the first step, the halogenated aryl compound is reacted with a diarylamine having at least one protected oxygen functional group, such as in the presence of a suitable catalyst. The diarylamine having at least one protected oxygen functional group may be any diarylamine with one or more protected oxygen functional groups attached to one or both of the aryl groups, for example methoxydiphenylamine. The protected oxygen functional group may be comprised of any suitable alkyl group from 1 to about 20 carbon atoms, tetrahydropyranyl group, or trialkylsilyl group.

The catalyst used in the first step may be, for example, a transition metal catalyst containing Pd, Fe, Ni, or Cu. The reaction typically takes place in the presence of a base, which can be any suitable base. The catalyst is also not particularly limited, and suitable catalysts include those that are known or discovered to be useful for formation of nitrogen-carbon bonds. For example, suitable catalysts include ligated palladium catalysts, such as those disclosed by Buchwald et al. and Hartwig et al. (see, e.g., *J. Org. Chem.* 2000, 65, 5327-5333, the entire disclosure of which is incorporated herein by reference), ligated nickel catalysts, such as those disclosed by Chen and Yang (see, e.g., *J. Org. Chem.* 2007, 72, 6325, the entire disclosure of which is incorporated herein by reference), or ligated iron and copper catalysts, such as those disclosed by Taillefer et al. (see, e.g., *Angew. Chem. Int. Ed.* 2007, 46, 934, the entire disclosure of which is incorporated herein by reference).

Any suitable base may be used in embodiments, such as an alkaline hydroxide or an alkaline alkoxide and the like. Exemplary bases that may be used in embodiments include bases having the general formula MOR, in which O is oxygen, M is a metal atom, and R is a hydrogen or an alkyl group. M is a metal selected from potassium, sodium, lithium, calcium, magnesium and the like; and R is a hydrogen or a straight or branched alkyl group selected from methyl, ethyl, propyl, butyl, pentyl, hexyl, heptyl, octyl, nonyl, and decyl groups, such as methyl, ethyl, n-propyl, isopropyl, n-butyl, isobutyl, tert-butyl, octyl, decyl and the like. Suitable bases include potassium hydroxide, potassium tert-butoxide, sodium tert-butoxide, and sodium tert-pentoxide.

In an embodiment of the present disclosure, an example of a suitable catalyst is palladium acetate ligated with tri-tert-butylphosphine in the presence of a base. One specific suitable catalyst is 2,4,6-trioxa-1,3,5,7-tetramethyl-8-phosphaadamantane, which is manufactured as Cytop-216 (Cytec Industries). However, it will be apparent to those skilled in the art that other ligands, such as any tertiary phosphone ligand such as biaryldialkylphosphine or trialkyl phosphine ligands, or N-heterocyclic carbene complexes could also be used to produce suitable results (from the point of view of conversion and yield), and thus would be suitable to ligate palladium or other metals and thus act as catalysts for the process described in this disclosure.

The reaction of the first step of the process can be carried out in the presence of the catalyst, and can be conducted in continuous mode. However, the reaction may be conducted in bath mode. For example, the reaction can be carried out for a period of from about 30 minutes to about 30 hours or more, such as a reaction time of from about 30 minutes to about 12 hours.

The reaction of the first step of the process can be carried out in a suitable solvent, such as toluene, xylene, decane, tetrahydrofuran, dioxane, other organic solvents, or mixtures thereof. The choice of solvent can be decided based on the solubility of the starting materials, intermediates, and final products, and will be readily apparent or within routine experimentation to those skilled in the art. Furthermore the choice of solvent can be decided based on the desired operating temperature range. The described process is exothermic and precautions should be taken to ensure that the solvent chosen is capable of dispersing the produced heat by, for example, refluxing and cooling at such a rate so as to control the exotherm. The reaction is desirably conducted under an atmosphere of inert gas (such as nitrogen or argon, which excludes substantially all oxygen and other reactive gasses from the reactor) so as to preclude deactivation of catalyst or base by oxygen or atmospheric moisture. Furthermore, the reaction of the second step may take place at, for example, a temperature of about 20° C. to about 150° C.

In a second step, the resulting N,N,N',N'-(tetraaryl)-aryl-diamine containing at least two protected oxygen functional groups is reacted with a suitable deprotecting agent. The deprotecting agent may be any known alkyl arylether deprotecting agent, for example 2-(diethylamine)-ethanethiolate. Other suitable deprotecting agents include boron trihalides such as boron trifluoride, boron trichloride, and boron tribromide and alkylsilylhalides such as trimethylsilyl chloride and trimethylsilyl iodide. The deprotecting agent turns the ether groups into alcohol groups, thereby forming a N,N'-((hydroxy)$_m$-diaryl)-N,N'-((hydroxy)$_n$-diaryl)-aryl-diamine.

After each step is completed, suitable separation, filtration, and/or purification processes can be conducted, as desired to a desired purity level. For example, the desired N,N'-((hydroxy)$_m$-diaryl)-N,N'-((hydroxy)$_n$-diaryl)-aryl-diamine product can be subjected to conventional organic washing steps, can be separated, can be decolorized (if necessary), treated with known absorbents (such as silica, alumina, and clays, if necessary) and the like. The final product can be isolated, for example, by a suitable recrystallization procedure. The final product can also be dried, for example, by air drying, vacuum drying, or the like. All of these procedures are conventional and will be apparent to those skilled in the art.

The N,N'-((hydroxy)$_m$-diaryl)-N,N'-((hydroxy)$_n$-diaryl)-aryl-diamine produced by this process can be further processed and/or reacted to provide other compounds for their separate use. For example, the N,N'-((hydroxy)$_m$-diaryl)-N,N'-((hydroxy)$_n$-diaryl)-aryl-diamine can be further processed

EXAMPLES

The disclosure will be illustrated in greater detail with reference to the following Example, but the disclosure should not be construed as being limited thereto. In the following example, all the "parts" are given by weight unless otherwise indicated.

Example

Bromination of Aryl Compound

In a 2 L 3-necked flask equipped with a thermometer, mechanical stirrer, reflux condenser and scrubber was placed 1.6 L of trichlorobenzene. To this was added 100 g of p-terphenyl and 100 mg of iodine. This mixture was stirred for 10 minutes at a temperature of roughly 22° C., after which 45 mL of bromine was added. The mixture was next heated at about 100° C. for 1 hour, while being stirred. The mixture was then cooled, and methanol was added to trigger precipitation. The precipitate was collected by filtration and washed with methanol. Finally, the product was dried under vacuum to give a white powder in 69% yield.

Palladium-Catalyzed Cross-Coupling

A 2-necked, 2000 mL RBF equipped with mechanical stirrer was flame-dried and cooled under an argon atmosphere. Pd(OAc)$_2$ (1.74 g, 7.75 mmol) was added to the reactor followed by toluene (700 mL) which resulted in an orange, homogeneous solution. A solution of P(t-Bu)$_3$ in toluene (0.025 M, 309 mL) was added by syringe in 50 mL portions and the mixture was stirred under an argon atmosphere for 10 min at which time a golden yellow solution resulted. Dibromoterphenyl (100 g, 258 mmol) was added and the resulting suspension was stirred for 5 min. 3-methyldiphenylamine (105 g, 528 mmol) was added and the suspension was stirred for 5 min. NaOt-Bu (61.9 g, 644 mmol) was added and a reflux condenser was placed on the reactor. The reaction was heated to reflux (heating mantle set temperature was 125 C, took 30 min to reach reflux) and the reaction was monitored by HPLC. The reaction was complete after about 60 min at reflux. The reaction was filtered hot and the filtrate was concentrated to afford a yellow solid. The yellow solid was suspended in a hot mixture of acetone/water, filtered, and the filtercake was dried in a vacuum oven to afford the N,N'-diaryl-N,N'-di(alkyl-oxyaryl)-aryl-diamine product as a yellow solid (140 g, 87%).

Deprotection

Sodium t-butoxide (194 g, 2.02 mol) was added in portions over 10 min to a stirred suspension of 2-(diethylamino)-ethanethiol hydrochloride (150 g, 0.96 mol) in N-methylpyrrolidone (1.4 L). A bright pink color resulted. The mixture was stirred for 15 min at about 22° C., the N,N'-diaryl-N,N'-di(alkyl-oxyaryl)-aryl-diamine (200 g, 0.32 mol) was added, and the reaction was heated to 140° C. The reaction became homogeneous and was a dark yellow/green colour. The reaction was monitored by HPLC and was complete after about 2.5 h. The reaction was cooled to about 22° C. and MeOH (1400 mL) was added followed by controlled addition of HCl (2 M, aq, 1020 mL). Upon addition of HCl a pale-yellow precipitate formed. Once all of the acid was added the mixture was stirred for 10 min. The precipitate was collected by filtration through a fiber-glass filter and air dried to afford a pale yellow solid. The yellow solid was dissolved in THF (800 mL) and transferred to a separatory funnel. The organic phase was washed with 1:1 water/brine (4×800 mL), dried (MgSO$_4$), filtered, and concentrated to afford an off-white solid. The crude reaction product was placed in a 3 L flask equipped with mechanical stirring and Dean Stark apparatus with a thermometer and heated in heptane (total volume ~1.5 L). Solvent was removed until the distillate temperature remained 98° C. for over 30 min. The suspension was then cooled to rt, filtered, and dried in a vacuum oven overnight to afford the N,N'-diaryl-N,N'-di(hydroxyaryl)-aryl-diamine product, N,N'-diphenyl-N,N'-di(3-hydroxyphenyl)-terphenyl-diamine (187 g, 98%).

What is claimed is:

1. A process for forming a N,N'-((hydroxy)$_m$-diaryl)-N,N'-((hydroxy)$_n$-diaryl)-aryl-diamine compound, where m and n are each integers having a value from 0 to 2 inclusive and the value of m+n is at least 1, comprising
   (1) reacting a halogenated aryl compound with a diarylamine having at least one protected oxygen functional group in the presence of a catalyst to form an N,N,N',N'-(tetraaryl)-aryl-diamine containing at least two protected oxygen functional groups; and
   (2) reacting the N,N,N',N'-(tetraaryl)-aryl-diamine with a deprotecting agent to form a N,N'-((hydroxy)$_m$-diaryl)-N,N'-((hydroxy)$_n$-diaryl)-aryl-diamine;
   wherein the catalyst is palladium ligated with 2,4,6-trioxa-1,3,5,7-tetramethyl-8-phosphaadamantane.

2. The process of claim 1, wherein the halogenated aryl compound, the diarylamine having at least one protected oxygen functional group, the N,N,N',N'-(tetraaryl)-aryl-diamine containing at least two protected oxygen functional groups, and the N,N'-((hydroxy)$_m$-diaryl)-N,N'-((hydroxy)$_n$-diaryl)-aryl-diamine are represented as follows:
   (1) X—Ar$^1$—X+((R$^1$O)$_m$—Ar$^2$)—NH—(Ar$^3$—(OR$^1$)$_n$) →((R$^1$O)$_m$—Ar$^2$)(Ar$^3$—(OR$^1$)$_n$)—N—Ar$^1$—N—((R$^1$O)$_n$—Ar$^3$)(Ar$^2$—(OR$^1$)$_m$)
   (2) ((R$^1$O)$_m$—Ar$^2$)(Ar$^3$—(OR$^1$)$_n$)—N—Ar$^1$—N—((R$^1$O)$_n$—Ar$^3$)(Ar$^2$—(OR$^1$)$_m$)→((HO)$_m$—Ar$^2$)(Ar$^3$—(OH)$_n$)—N—Ar$^1$—N—((HO)$_n$—Ar$^3$)(Ar$^2$—(OH)$_m$)
   wherein:
   m is an integer having a value from 0 to 2 inclusive
   n is an integer having a value from 0 to 2 inclusive, where the value of m+n is at least 1;
   X represents a halogen (Cl, Br, I);
   R$^1$ represents an alkyl group of from 1 to about 20 carbon atoms, a tetrahydropyranyl group, or a trialkylsilyl group;
   Ar$^1$, Ar$^2$ and Ar$^3$ which can be the same or different, are selected from the group consisting of tri-, di- or mono-substituted or unsubstituted aromatic components, and substituted or unsubstituted aryl groups having from 2 to about 15 conjugate bonded or fused benzene rings, wherein a substituent on the aryl groups Ar$^1$, Ar$^2$ and Ar$^3$ is one or more of the group consisting of hydrogen, a halogen, an alkyl group having from 1 to about 20 carbon atoms, a hydrocarbon radical having from 1 to about 20 carbon atoms, an aryl group, an aryl group substituted by one or more alkyl groups, an alkyl group containing a heteroatom and having from 1 to about 20 carbon atoms, a hydrocarbon radical containing a heteroatom and having from 1 to about 20 carbon atoms, an aryl group containing a heteroatom, and an aryl group containing a heteroatom substituted by one or more alkyl groups.

3. The process of claim 1, wherein the first step is a transition metal catalyzed coupling of a halogenated aryl compound and a diarylamine.

4. The process of claim 1, wherein the first step further comprises a base.

5. The process of claim 4, wherein the base is a metal alkoxide.

6. The process of claim 1, wherein the deprotecting agent is an alkyl or arylthiolate.

7. The process of claim 1, wherein the deprotecting agent is 2-(diethylamino)-ethanethiolate.

8. The process of claim 1, wherein the first step is carried out under an inert atmosphere.

9. The process of claim 8, wherein the inert atmosphere is nitrogen or argon gas.

10. The process of claim 1, wherein the first step is carried out in a non-polar solvent.

11. The process of claim 10, wherein the non-polar solvent is selected from the group consisting of toluene and xylene.

12. The process of claim 2, wherein $Ar^1$ is selected from the group consisting of biphenyl and terphenyl.

13. The process of claim 12, wherein $Ar^1$ is p-terphenyl.

14. The process of claim 2, wherein $Ar^2$ and $Ar^3$ are phenyl groups.

15. The process of claim 1, wherein the halogenated aryl compound is formed by reacting bromine with an aryl compound, in the presence of a trace of iodine and in a trichlorobenzene solvent at 100° C.

16. A process for forming a N,N'-diphenyl-N,N'-bis(3-hydroxyphenyl)-[1,1':4'1"-terphenyl]-4,4"-diamine compound, comprising
   (1) reacting dibromoterphenyl with 3-methoxydiphenylamine in the presence of a ligated palladium catalyst and a base, and
   (2) reacting the resulting N,N'-diphenyl-N,N'-bis(3-hydroxyphenyl)-[1,1':4'1"-terphenyl]-4,4"-diamine with a thiolate deprotecting agent;
   wherein the ligated palladium catalyst is palladium ligated with 2,4,6-trioxa-1,3,5,7-tetramethyl-8-phosphaadamantane.

17. A process for forming a N,N'-diphenyl-N,N'-di(3-hydroxyphenyl)-biphenyl-diamine compound, comprising
   (1) reacting dibromobiphenyl with 3-methoxydiphenylamine in the presence of a ligated palladium catalyst and a base, and
   (2) reacting the resulting N,N'-diphenyl-N,N'-di(3-methoxyphenyl)-biphenyl-diamine with a thiolate deprotecting agent;
   wherein the ligated palladium catalyst is palladium ligated with 2,4,6-trioxa-1,3,5,7-tetramethyl-8-phosphaadamantane.

* * * * *